United States Patent [19]

Garito

[11] Patent Number: 4,615,962
[45] Date of Patent: Oct. 7, 1986

[54] DIACETYLENES HAVING LIQUID CRYSTAL PHASES

[75] Inventor: Anthony F. Garito, Radnor, Pa.

[73] Assignee: University Patents, Inc., Norwalk, Conn.

[21] Appl. No.: 526,033

[22] Filed: Aug. 24, 1983

Related U.S. Application Data

[63] Continuation-in-part of Ser. No. 340,471, Jan. 18, 1982, Pat. No. 4,439,514, which is a continuation of Ser. No. 113,552, Jan. 21, 1980, abandoned, which is a continuation-in-part of Ser. No. 52,007, Jun. 25, 1979, abandoned. Continuation-in-part of Ser. No. 129,560, Mar. 12, 1980, Pat. No. 4,431,263, which is a continuation-in-part of said Ser. No. 52,007, Jun. 25, 1979.

[51] Int. Cl.$^4$ ............................................. G03C 1/68
[52] U.S. Cl. ........................................ 430/20; 430/18; 430/270; 430/272; 430/935; 427/53.1; 427/54.1; 526/285; 522/182; 522/63
[58] Field of Search ............... 430/20, 18, 270, 935, 430/272; 427/53.1, 54.1; 526/285; 204/157.1 R, 159.23, 159.24; 522/182, 63

[56] References Cited

U.S. PATENT DOCUMENTS

| | | | |
|---|---|---|---|
| 3,300,456 | 1/1967 | Hay | 526/135 |
| 3,501,297 | 3/1970 | Cremeans | 430/338 |
| 3,501,302 | 3/1970 | Foltz | 430/270 |
| 3,501,303 | 3/1970 | Foltz et al. | 430/270 |
| 3,501,308 | 3/1970 | Adelman | 430/270 |
| 3,594,175 | 7/1971 | Hay | 430/270 |
| 3,679,738 | 7/1972 | Cremeans | 430/270 |
| 3,702,794 | 11/1972 | Hartlein | 156/310 |
| 3,723,121 | 3/1973 | Hauser | 430/20 |
| 3,743,505 | 7/1973 | Bloom et al. | 430/20 |
| 3,767,415 | 10/1973 | Tanaka | 430/287 |
| 3,772,011 | 11/1973 | Guevera et al. | 430/270 |
| 3,772,027 | 11/1973 | Luckey | 430/495 |
| 3,772,028 | 11/1973 | Fico et al. | 430/195 |
| 3,794,491 | 2/1974 | Borsenberger et al. | 430/20 |

(List continued on next page.)

FOREIGN PATENT DOCUMENTS

| | | |
|---|---|---|
| 0036899 | 3/1980 | European Pat. Off. |
| 0041184 | 5/1981 | European Pat. Off. |
| 925290 | 3/1955 | Fed. Rep. of Germany . |
| 1154191 | 6/1969 | United Kingdom . |
| 1344040 | 1/1974 | United Kingdom . |

OTHER PUBLICATIONS

Shishmakova et al.: Chem. Abst. 17452g, vol. 64, 1966.
Chemical Abstracts, vol. 65, No. 10, Nov. 7, 1966, Columbus, Ohio, U.S.A.
I. L. Kotlyarevskill et al., "Highly Unsaturated Polymer. XVII. Synthesis of Mono- and Diethyinylvinyl Derivatives of Benzene and Their Oxidative Condensation" col. 15 253, Abstract No. 15 253d. & Izy, Akad. Nauk SSSR., Ser. Khim 1966(2), 360-2.
Chemical Abstracts, vol. 64, No. 12, Jun. 6, 1966, Columbus, Ohio, U.S.A.
T. G. Shishmakova et al., "Synthesis of (Phenylvinyl) Acetylenes from Unsaturated Ketones" col. 17 452, Abstract No. 17 452g & Izv. Akad. Nauk SSSR, Ser. Khim. 1966(2), 360-2.
Chemical Abstracts, vol. 51, No. 21, Nov. 10, 1957, Columbus, Ohio, U.S.A.
F. Bohlmann et al., "Polyacetylene Compounds. XIX.

(List continued on next page.)

Primary Examiner—Won H. Louie
Attorney, Agent, or Firm—Woodcock Washburn Kurtz Mackiewicz & Norris

[57] ABSTRACT

Dialkenyl diacetylenes, especially divinyl diacetylenes having liquid crystalline phases, are provided. In accordance with certain preferred embodiments, diacetylenes having liquid crystalline phases are provided which may be polymerized while in the liquid crystalline state to yield conjugated polymers. The processes for the polymerization of such liquid crystalline diacetylenes and for the elaboration of useful optical, electro-optical, electro-acoustic, mechanical, thermal, structural, waveguiding and other articles are also disclosed.

13 Claims, 4 Drawing Figures

U.S. PATENT DOCUMENTS

| | | | |
|---|---|---|---|
| 3,811,895 | 5/1974 | Ehrlich | 430/495 |
| 3,822,134 | 7/1974 | Rasch | 430/539 |
| 3,832,580 | 8/1974 | Yamamuro et al. | 310/9.5 |
| 3,840,369 | 10/1974 | Carlick et al. | 430/495 |
| 3,844,791 | 10/1974 | Bloom et al. | 430/336 |
| 3,911,169 | 10/1975 | Lesaicherre | 430/272 |
| 3,923,622 | 12/1975 | Baughman et al. | 430/20 |
| 3,945,831 | 3/1976 | Satomura | 430/287 |
| 3,994,867 | 11/1976 | Baughman et al. | 528/481 |
| 3,999,946 | 12/1976 | Patel et al. | 23/253 |
| 4,066,676 | 1/1978 | Bloom et al. | 430/495 |
| 4,103,045 | 7/1978 | Lesaicherre | 430/319 |
| 4,125,534 | 11/1978 | Yee | 260/315 |
| 4,154,638 | 5/1979 | Franz et al. | 156/326 |
| 4,164,458 | 8/1979 | Patel | 204/159.17 |
| 4,168,982 | 9/1979 | Pazos | 430/281 |
| 4,189,399 | 2/1980 | Patel | 252/408 |
| 4,195,055 | 3/1980 | Patel | 422/56 |
| 4,195,056 | 3/1980 | Patel | 422/56 |
| 4,195,057 | 3/1980 | Patel | 422/56 |
| 4,195,058 | 3/1980 | Patel | 422/56 |
| 4,208,186 | 6/1980 | Patel | 23/230 |
| 4,208,501 | 6/1980 | Yee | 526/259 |
| 4,215,208 | 7/1980 | Yee et al. | 526/285 |
| 4,220,747 | 9/1980 | Preziosi et al. | 560/24 |

OTHER PUBLICATIONS

Nucleophilic Addition to Polynes" col. 16 273, Abstract No. 16 273h & Ann. 604, 207-13 (1957).
Chemical Abstracts, vol. 45, No. 5, Mar. 10, 1951, Columbus, Ohio, U.S.A.
R. T. Holman, et al. "Spectral and Oxidation Studies on Matricaria Ester (2, 8–Decadiene-4, 6–Diynoic Acid Methyl Ester)" p. 1951, Abstract No. 2 398b & Acta Chem. Scand. 4, 416-21 (1950).
Chemical Abstracts, vol. 46, No. 12, Jun. 25, 1952, Columbus, Ohio, U.S.A.
"X-Ray Optics: Applications to Solids" (Ed. H. J. Queisser).
"X-Ray Lithography", E. Spiller and R. Feder, pp. 35-92, Springer (1977).
"Polymer Resist Systems for Photo and Electron Lithography", L. F. Thompson and R. E. Kerwin, Ann. Rev. Mat. Sci., vol. 6, pp. 267-301.
Photo-Resist Materials and Processes by William DeForest, McGraw-Hill, 1975.
Science, vol. 196, No. 4293, pp. 945-949, May 27, 1977, by R. W. Keyes.
"Fabrication Techniques for Surface-Acoustic-Wave and Thin-Film Optical Devices", IEEE, vol. 62, No. 10, pp. 1361-1387, Oct. 1974, Henry I. Smith.
Khimii article Russian Chemical Reviews, vol. 32, No. 5, pp. 229-243 (1963).
Bohlmann article Angewandte Chemie, vol. 65, No. 15, pp. 385-408 (1953).
"Synthesis of Chiral Diacetylene Polymers", Garito et al., Makromolecular Chemie (in press).
"The Chemistry of Diacetylenes", Keter Pub. House, Jerusalem (1974).
"Synthesis of Nitrophenoxymethyl Substituted Diacetylene Monomers", Kalyanaraman et al., Makromolecular Chemie, vol. 180, Jun. 1979.
Strauss, et al., Ber. 63B, 1868 (1930).
Monomolecular Resists: A New Class of High Resolution Resists for Electron Beam Bicrolithography", Solid State Tehnology, Aug. 1979, Barraud et al.
"Solid-State Electron-Induced Polymerization of Omega-Tricosenoic Acid Multilayers", Journal of Colloid and Interface Science, 62, No. 3, Dec. 1977, Barraud et al.
"Solid-State Synthesis and Properties of the Polydiacetylenes", Baughman et al., Annals of N.Y. Academy of Science, vol. 313 (1978).
"Polymerization of Diacetylene Carbonic Acid Monolayers at the Gas-Water Interface", Day et al., J. Polymer Sciences, Polymer Letters Ed., vol. 16, p. 205 (1978).
"Kinetics of Thermal Polymerization in the Solid State: 2,4–Hexadiyne-1,6 Diol Bis(p-Toluene Sulfoneate)", Garito et al., J. Polymer Sci., vol. 16, pp. 335-338 (1978).
"Kinetics of Solid State Polymerization of 2,4–Hexadiyne-1,6-Diol-Bis(p-Toluene Sulfonate)", Garito et al., Molecular Metals, Hatfield Ed. (Plenum, 1979).
"Recent Progress in the Chemistry and Physics of Poly(diacetylenes)", Wegner, Molecular Metals, W. E. Hatfield Ed., Plenum (1979).
"Polymerization of Diacetylenes in Multi-Layers", Wegner et al., Journal of Polymer Science, Polymer Chemistry Ed., vol. 17, pp. 1631-1644 (1979).
"The Quantum Yield of the Topochemical Photopolymerization of Diacetylenes in Multi-Layers", by Wegner et al., Makromolecular Chemistry, vol. 179, pp. 1639-1642 (1978).
"Mechanism of Adhesion Through Silane Coupling Agents", E. P. Plueddemann, Composite Materials, Brautman, Krock Eds., vol. 6, Ch. 6, Academy Press (1974).
Chodkiewicz, W. Ann. Chem., (Paris) 2, 853 (1957).
*Dictionary of Organic Compounds*, vol. 3, p. 1889.
*Chemical Abstracts*, vol. 63, Number 3309 D (1965).
Chemistry of the Higher Fungi, Part X, Further Polyacetylenic Derivatives of Decane from Various Basidiomycetes by J. N. Gardner, E. R. H. Jones, P. R. Leeming, and J. S. Stephenson, Journal of the Chemical Society (1960), pp. 691-697.
Konstitution and Lichtabsorption symmetrischer und unsymmekirscher Polyin-ene Sowie Synthese Eines Kohlenwasserstoffs aus Centaurea-Arten by Ferdinand Bohlmann and Peter Herbst, Chemische Berichte, vol. 91, pp. 1631-1642.
The Molecular Physics of Liquid-Crystal Devices, Physics Today, May 1982, pp. 66-74.
Polymeric Liquid Crystals, Samulski, Physics Today, May 1982, pp. 40-46.
Optical Nonlinearities in One-Dimensional-Conjugated Polymer Crystals; Baughman et al., 4/19/76; vol. 36, No. 16.
H. H. Anderson, "Tri-n-Butylgermanium Esters, Halides, Isocyanate and Oxide", Abstract No. 5 525b & Chem. Soc. 73, 5800-2 (1951).
Physics Today, vol. 35, No. 5, May 1982, E. T. Samulsi, "Polymeric Liquid Crystals", pp. 40-46.
Physics Today, vol. 35, No. 5, May 1982, F. J. Kahn, "The Molecular Physics of Liquid-Crystal Devices", pp. 66-74 (p. 70, left column, line 30-right column, line 16; p. 73, left column, line 45-right column, line 39).

DIACETYLENES HAVING LIQUID CRYSTAL PHASES

Portions of this work have been supported by the Defense Advanced Research Projects Agency, Grant No. DAAK-70-77-C-0045 (5-26502). The United States Government has certain rights in this invention.

CROSS-REFERENCED TO RELATED APPLICATIONS

This application is a continuation in part of Ser. No. 340,471, filed Jan. 18, 1982, U.S. Pat. No. 4,439,514 which is a continuation of Ser. No. 113,552 filed Jan. 21, 1980, abandoned which is a continuation in part of Ser. No. 052,007 filed June 25, 1979 abandoned. This application is also a continuation in part of Ser. No. 129,560 filed Mar. 12, 1980, U.S. Pat. No. 4,431,263 which is a continuation in part of Ser. No. 052,007 filed June 25, 1979. Each of the foregoing applications are incorporated herein by reference as though fully set forth.

BACKGROUND OF THE INVENTION

This invention is directed to certain diacetylenes which exhibit liquid crystalline phases or states. This invention is also directed to methods for the polymerization of such liquid crystal diacetylenes, to polymerized articles produced therefrom and to methods for the employment of such polymerized or polymerizable materials as optical, acoustical, electronic, electro-optical, electro-acoustic, mechanical, thermal, conductive, piezoelectric, pyroelectric and many other components or devices.

As described in those applications from which this application depends, diacetylenes have been known and their properties somewhat explored. Certain divinyl diacetylenes have been reported in connection with research into natural products. See Gardner et al., "Chemistry of the Higher Fungi, Part X, Further Polyacetylenic Derivatives of Decane from Various Basidiomycetes", *Journal of the Chemical Society*, (1960), pp. 691–697; and Bohlmann, et al., "Konstitution und Lichtabsorption Symmetrischer und unsymmekirscher Polyin-ene Sowie Synthese Eines Kohlenwasserstoffs aus Centaurea-Arten", *Chemische Berichte*, Vol. 91, pp. 1631–1642. No diacetylene has previously been identified as having a liquid crystalline phase or state, and no dialkenyl diacetylene has been known to be polymerizable. Moreover, the polymerization of diacetylenes including dialkenyl diacetylenes, especially divinyl diacetylenes, while they are in the liquid crystalline state, has not been known heretofore.

SUMMARY OF THE INVENTION

It has been found that certain diacetylenes may be formulated which exhibit liquid crystalline states or phases. Such liquid crystalline phase-possessing diacetylenes have been found which are useful in bulk and polymerizable in bulk to form useful mechanical, structural, conductive, thermal and other polymerized materials. It has also been found that layers of certain diacetylenes exhibiting liquid crystal phases may be elaborated upon suitable substrates, caused to assume a liquid crystal state, and polymerized in the liquid crystal state to form useful optical, electro-optical, electro-acoustical, mechanical, thermo-stable, conductive and other articles. In accordance with another embodiment, a layer of liquid crystalline diacetylene is surmounted by two substrate layers. In accordance with another, preferred embodiment, the liquid crystalline diacetylene layer may be caused to assume a regular orientation either by covalently bonding to the substrate or substrates through the intermediation of coupling agent molecules, or CAMs, through non-bonded enforcement of order via CAM surface modification, through surface grooving, or otherwise. See Kahn, "The Molecular Physics of Liquid-Crystal Devices". *Physics Today*, May 1982, pp. 66–74, which is incorporated herein by reference.

In accordance with other embodiments, the diacetylene layer or bulk-form diacetylene-containing material may be caused to assume a liquid crystalline state and polymerized in that state either entirely or in an imagewise fashion. Through judicious selection of liquid crystalline diacetylene molecules, or by the incorporation of certain non-liquid crystalline molecules compatible with the liquid crystalline diacetylene molecules, it is possible to prepare polymerized articles having numerous useful properties.

The diacetylene-containing compositions of this invention may also be polymerized in bulk such as in a form, mold, capillary or otherwise. The resulting polymer is believed to be useful for a wide variety of structural, thermal, electrical, waveguiding, and other uses. It is believed that a wide variety of processing schemes may be employed to manipulate these polymers including casting, molding, sheet forming, extrusion and the like. "Polymeric Liquid Crystals", Samulski, *Physics Today*, May 1982, pp. 40–46 is incorporated by reference to illustrate certain other uses of the polymers of this invention.

It is also believed that liquid crystalline diacetylenes in accordance with this invention may serve as "hosts" for incorporation of "guest" molecules. Thus, liquid crystal or non-liquid crystalline guest molecules having useful properties such as non-centrosymmetry, a different absorption spectrum, good mechanical, thermal, processing or other physical properties, and other benefits may be caused to assume liquid crystalline behavior by association or admixture with an effective amount of a liquid crystalline diacetylene. Further explanation of the host-guest phenomenon is provided by Dewar, et al., *Journal of Organic Chemistry*, Vol. 35, pp. 2711 et seq. (1970).

In accordance with other embodiments, liquid crystal diacetylenes may be employed without polymerization thereof as, for example, in display and other devices and for all of the many other uses known to those skilled in the art. See, for example, the Kahn article in *Physics Today* incorporated herein by reference.

OBJECTS OF THE INVENTION

It is an object of the present invention to prepare diacetylenes having one or more liquid crystalline phases.

Is is another object of the present invention to prepare polymerizable dialkenyl diacetylenes, especially polymerizable divinyl diacetylenes.

A further object of the present invention is to provide materials comprising diacetylenes having liquid crystalline phases which can be polymerized in the liquid crystalline state.

A still further object is to provide liquid crystalline diacetylene materials which exhibit a sensible, non-linear optical effect.

A further object is to provide methods for the polymerization of certain diacetylenes which exhibit liquid crystalline states by causing then to assume a liquid crystalline state and to undergo polymerization while in that state.

Another object is to provide bulk polymerizable diacetylenes suitable for plastics processing.

In accordance with further objects, polymerized articles are provided for optical, electro-optical, electroacoustical, mechanical, structural, thermal, conductive, and other uses.

Yet another object provides diacetylenes having liquid crystalline phases which are suitable for use in displays or the like.

The preparation of articles comprising one or more substrates and one or more layers of compositions comprising liquid crystalline diacetylenes in either the polymerized or unpolymerized state is also an object of the present invention.

The foregoing assemblages of substrate and liquid crystalline diacetylene are also provided in accordance with further objects of the invention wherein the diacetylene is oriented inter se with respect to one or more of the substrates.

A further object is to provide liquid crystalline diacetylenic materials which may be polymerized in an imagewise fashion.

Still further objects will become apparent to those of ordinary skill in the art from a review of the present specification.

DETAILED DESCRIPTION OF THE INVENTION

The present invention provides dialkenyl diacetylenes, especially divinyl diacetylenes, and certain diacetylenes having liquid crystalline states or phases. Dialkenyl diacetylenes in accordance with this invention may be represented by the following formula:

While those of ordinary skill in the art will appreciate that a very wide variety of substituent "R" groups may be selected in order to vary the basic structure of dialkenyl diacetylenes, certain groups are presently viewed as having the greatest likelihood of providing one or more of the properties described in connection with the present invention. Accordingly, it is preferred that dialkenyl diacetylenes in accordance with the foregoing formula be provided wherein $R_1$ and $R_2$ may be the same or different and are selected from the group consisting of H, cyano, halogen and alkyl having from 1 to about 3 carbon atoms; wherein $R_3$ and $R_4$ may be the same or different and are selected from the group consisting of H, cyano, halogen, amino, aryl and alkyl having from 1 to about 6 carbon atoms and wherein $R_5$ and $R_6$ may be the same or different and are selected from the group consisting of H, alkyl, aryl, aralkyl, alkaryl and heterosubstituted alkyl and aryl having from 1 to about 30 carbon atoms. It is also presently thought possible for one or more of the groups $R_1$, $R_2$, $R_3$ and $R_4$ to comprise further ethylenic unsaturation either in or out of conjugation with the indicated double bonds and diacetylene structure.

It is generally believed that liquid crystalline materials should have molecular structures having a high aspect ratio. In this regard, rigid, rod-like molecules having anisotropic polarizability are believed to be preferable. Accordingly, it is presently believed that molecules having the following formula may be preferred:

wherein $R_5$ and $R_6$ have the meanings attributed previously.

Those molecules presently known to exhibit liquid crystalline phases belong to the class of diacetylenes represented by the following formula:

wherein $R_7$ and $R_8$ may be the same or different and are selected from the group consisting of H; cyano; halogen; amino; nitro; hydroxyl; sulfoxyl; sulfonyl; and alkyl, aryl, alkaryl, or aralkyl having from about 1 to about 24 carbon atoms. In the foregoing formulas, $R_5$, $R_6$, $R_7$ and $R_8$ may also likely include numerous other substituents such as hydroxyl, sulfhydryl, amino, acid ester, amide, sulfamide, halo etc.

Those molecules which have presently been found to exhibit liquid crystalline behavior may preferably be represented by the following formula:

wherein $R_9$ is alkyl having from about 1 to about 24 carbon atoms.

As will be appreciated by those having ordinary skill in the art, the dialkenyl diacetylenes which are prepared in accordance with the present invention may assume cis-trans and syn-anti isomerisms. It is presently believed that, a priori, each of the possible forms may be suitable for use in connection with one or more embodiments of the present invention. Mixtures of isomeric forms may also be useful. Additionally, mixtures of different diacetylenes may also be emmployed.

Dialkenyl diacetylenes may be synthesized by the coupling of monovinyl acetylenes such as through the Chodkowicz, Glaser or other reactions described in those applications from which this application depends and which have been incorporated by reference herein. The corresponding monovinyl acetylenes may be synthesized through the addition of pyridazine-1-oxide to the Grignard derivative of the desired haloaryl compound or through a Wittig reaction, as explained more fully in the examples.

Certain of the derivatives prepared were found to exhibit liquid crystalline behavior. Among these are the p-alkylphenyl divinyl diacetylenes represented by the following formula:

wherein $R_9$ is alkyl comprising from about 1 to about 24 carbon atoms. The specific members of this class which have, to date, been prepared and tested include methyl, ethyl, propyl and butyl analogues. It is expected that the entire range of alkyl-, and probably substituted alkylphenyl derivatives will similarly exhibit liquid crystalline behavior.

Certain of the phenyl divinyl diacetylene compositions synthesized were found not to exhibit liquid crystalline behavior. These included the nitrophenyl-, napthenyl-, and biphenyl-divinyl diacetylenes. It is not yet clear whether the di-p-cyanophenyl and chlorophenyl divinyl diacetylenes exhibit liquid crystalline behavior.

It is also believed that certain monoalkenyl diacetylenes may also exhibit liquid crystalline behavior and polymerizability and that the same may be useful for the purposes set forth herein.

Those skilled in the art are readily familiar with the means for determining whether or not a particular chemical species has a liquid crystalline state or phase. In this regard, differential scanning calorimetry, DSC, which provides a graphical representation of heat loss or gain by the material in question as a function of temperature, is generally employed. For materials having a liquid crystal state, the initial negative peak in the DSC plot is shallow, representing a change in phase from solid to liquid crystal rather than from solid to liquid, glass, gas or decomposition products. The solid-liquid crystal transition is generally reversible. Other DSC phenomena may also be demonstrated, including additional transitions from one liquid crystalline state to another, from the liquid crystalline to the liquid state, etc. Liquid crystalline behavior is also indicated via optical microscopy. Liquid crystals exhibit viscous behavior and optical birefringence. A further discussion of the liquid crystal state in polymers and their precursors is presented in Blumstein, *Liquid Crystalline Order in Polymers*, Academic Press, New York (1978).

The differential scanning calorimetry of the para alkylphenyl divinyl diacetylenes in accordance with the present invention, however, illustrate additional, suprising, phenomena. In addition to the solid-liquid crystalline transition and, in some cases, additional liquid crystalline inter-phase transitions, the materials exhibit a substantial, exothermic DSC peak. This may be seen in FIG. 4 for the propyl analog. This substantial peak represents thermal polymerization of the diacetylene in the liquid crystalline stae. For further understanding of polymerization in accordance with the present invention, the *Physics Today* article of Samulski is illustrative.

The ability of liquid crystalline divinyl and dialkenyl diacetylenes to polymerize while in their liquid crystalline state is believed to be unique. No other liquid crystalline material has heretofore been known which has been able to be polymerized to yield polymers with conjugated backbone structures.

The ability to polymerize the liquid crystalline diacetylene materials in accordance with the present invention permits the preparation of numerous articles having great utility for optical, electro-optical, electro-acoustical, piezoelectric, mechanical, thermal, conductive, ionic conductive and many other purposes. More particularly, it is possible to prepare articles comprising polymerized or polymerizable liquid crystal diacetylenes which may exhibit wave-guiding, electro-optic, electro-acoustic, pyroelectric and numerous other phenomena. Non-linear optical, harmonic generating piezoelectric and numerous other properties may be evidenced by such materials. In this regard, each of those uses disclosed in connection with Ser. Nos. 129,560 and 113,552 may likely employ the liquid crystalline diacetylenes and other materials of the present invention to good advantage.

The liquid crystalline materials of the present invention may be polymerized while in the liquid crystalline state through exposure to heat or to initiating radiation. Such polymerization has been found to take place with great efficiency, stereoregularity, and maintenance of intermolecular orientation. Accordingly, polymerization of liquid crystalline diacetylenes from the liquid crystalline state permits, in some cases, the rapid elaboration of polymerizable films or layers upon substrates or otherwise for polymerization. It is also believed to be possible to polymerize such materials in an imagewise fashion. Accordingly, such imagewise processability may enable the present materials to participate in methods and to provide articles in accordance with methods and articles disclosed in Ser. No. 340,471. The likely ability to provide imagewise polymerization of the materials of the present invention will facilitate the elaboration of complex optical, electro-optical, electroacoustic etc. devices through simplified and straightforward micro-lithographic techniques.

In accordance with an embodiment of this invention, one or more layers of diacetylenes having a liquid crystalline phase is elaborated upon one or more substrates. In accordance with this preferred embodiment, the layers of diacetylene may be oriented as described by Kahn's *Physics Today* article by surface grooving or via coupling agent molecules, CAMs, either with or without covalent bonding of the diacetylene to the CAM. In addition to those CAMs disclosed in prior applications and by Kahn in the article which has been incorporated herein by reference, substituted organosilanes and related materials including siloxanes, silazanes, chlorosilanes and other materials are preferred. Such silaneous materials are especially suited for the bonding of diacetylenic materials to substrates when the substrates comprise metals, metal oxides, semiconductors, semiconductor oxides, glasses, silicons, quartzes and certain polymers.

It is believed that the employment of surface orientation to align diacetylenes in accordance with the present invention inter se and/or with regard to one or more substrates, facilitates the organization of liquid crystalline diacetylenes into stable, oriented, organized macroassemblages for further polymerization and/or other processing. While the use of CAMs for the physical control of solid surfaces including certain liquid crystalline materials has previously been known, the use in connection with diacetylenes has not been reported heretofore. Thus, it is now possible to prepare articles comprising one or more layers of diacetylene oriented through CAMs to surfaces of one or more substrates to provide many useful articles. Such articles may subsequently be processed to provide still other useful articles. The resulting assemblages or articles may be useful as display devices in accordance with the procedure described by F. J. Kahn in *Applied Physics Letter*, Vol. 22, p. 386 (1973). Those of skill in the art will recognize the numerous other uses of these techniques. Many other uses of oriented diacetylenes will also be apparent to those of ordinary skill in the art. In short, liquid crystal diacetylenes may be employed either with or without orientation and either in bulk, on a substrate or otherwise, in all ways presently known for the employment of liquid crystalline materials.

The ability of diacetylenic liquid crystalline materials in accordance with the present invention to be elaborated upon substrates, to be oriented inter se upon the substrates, and to be polymerized while in the oriented liquid crystalline state, is especially useful in view of the highly unique and useful electronic properties of diacetylenic materials. These properties, which are more fully discussed in Ser. No. 129,560 and in those other patent applications which have been incorporated herein by reference, permit electro-optic, electro-acoustic, mechanical, thermal, conductive, optical, and numerous other devices to be elaborated from diacetylenes. In accordance with the present invention, such elaboration may take place with improved convenience and with higher efficiencies.

In order to provide covalent bonding of the diacetylene to the substrate via CAM molecules it may, in some cases, be necessary to modify the diacetylenic molecule to provide a situs of activity for such bonding. Thus, covalent bonding to the substrate via aminosilanes will generally require the presence of a carboxylic acid or other suitable group at one terminus of the liquid crystalline diacetylene. Other modifications may be selected when other CAMs are desired for use in such covalent bonding, however.

In addition to the foregoing, the dialkenyl diacetylenes of the present invention may be seen to have unsaturations (the olefinic bonds) in conjugation with the diacetylene moiety of the diacetylene. Additionally, when further unsaturations such as phenyl rings are incorporated in the dialkenyl diacetylenes of the present invention, further electronic coupling to the diacetylenic backbone may be evidenced. It is presently believed through consideration of theoretical analysis of these systems, that the electronic properties manifested by diacetylenes in general will be even more apparent and will exist to higher degrees in further conjugated diacetylene materials such as those presently contemplated. Accordingly, such materials are believed to have substantially higher nonlinear optical coefficients than do diacetylenes not having further olefinic conjugation. These effects are maintained upon polymerization since resulting polymers have conjugated unsaturations along the polymer "backbones".

Liquid crystalline materials have a certain well-known ability to serve as "host" species for the inclusion of "guest" molecules, which "guest" molecules are not necessarily, themselves, liquid crystalline. Thus, in connection with the present invention, it is possible to include within liquid crystalline diacetylenic compositions, a substantial proportion and even, possibly, a major proportion, of liquid crystalline or non-liquid crystalline materials, having particularly desired properties. The resulting host-guest mixtures are formulated to have liquid crystalline properties. Among these preferred "guest" molecules, for example, are materials having substantial nonlinear optical coefficients, different optical absorption spectra, charge transfer, electronic or ionic doping, mechanical properties, etc. In this way, it is possible to employ liquid crystalline materials to carry into an overall liquid crystalline system or array, useful molecules such as those having nonlinear optical properties, and to incorporate such useful molecules in overall polymeric systems. Since many diacetylenes having substantial nonlinear optical coefficients, and other useful properties are known, such as those described in parent application Ser. No. 129,560, which has been incorporated herein by reference, and since such materials are expected to be well-received as "guest" molecules in arrays or assemblages of liquid crystalline diacetylenes, the present system is viewed as being an ideal one for the formation of electro-optic, electro-acoustic, waveguiding and other highly useful optical devices. Moreover, useful structural, display, thermostable, waveguiding, piezoelectric and other uses are possible. Even more preferred materials for inclusion as "guest" molecules in liquid crystalline diacetylenic organizations are, of course, useful materials which are, themselves, liquid crystalline. Nonlinear optical, liquid crystalline, diacetylenes will benefit from the presence of olefinic bonds in conjugation with the diacetylenic "backbone" of the polymerized or unpolymerized diacetylenes of this invention to result in improvement of the nonlinear optical efficiencies of such molecules. Similar considerations apply to many other potential guests.

Inorganic or organic dopant materials may also be included as guest species. Thus, for example, iodine, tetracyano quinodimethane and other dopants may likely be added to alter the conductivity of the liquid crystal material or resulting polymer. Other dopants may also be employed as well to modify, for example, electrical and/or ionic conductivity.

Figure 1:
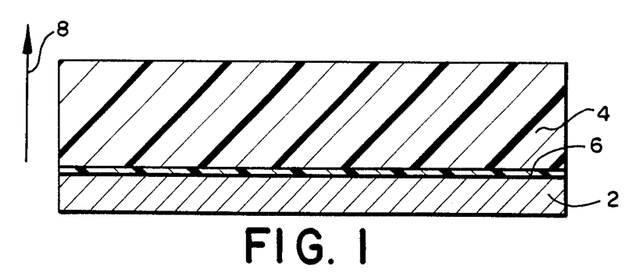
FIG. 1 depicts an article in accordance with an embodiment of the present invention comprising a substrate and a polymerized or polymerizable liquid crystalline diacetylene layer on the substrate oriented inter se by the intermediation of a layer of a coupling agent.

In accordance with the foregoing, reference is made to FIG. 1 depicting a substrate 2 overlaid with a layer of a liquid crystalline diacetylene 4. In accordance with a preferred embodiment, a CAM layer 6 is interposed between the diacetylene layer 4 and the substrate 2 to cause orientation of the layer 4 inter se and/or with respect to the substrate 2. In accordance with the embodiment, the assemblage of layer and substrate may be placed in an electric and/or magnetic field 8 to assist in the alignment of the diacetylene molecules for subsequent processing such as polymerization.

Figure 2:
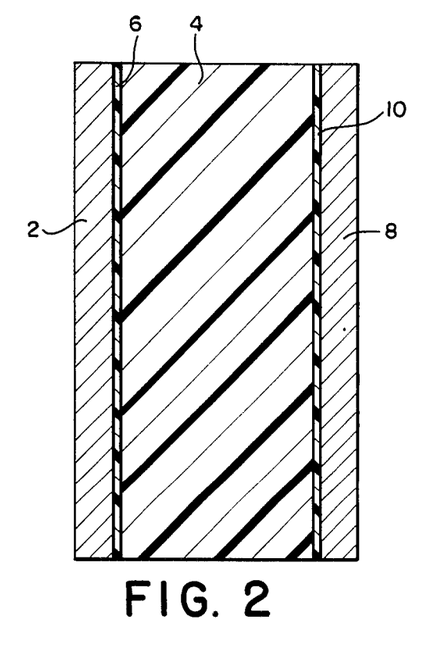
FIG. 2 depicts an article in accordance with another embodiment of the present invention wherein a second substrate surmounts the diacetylene layer of FIG. 1 and is in turn intermediated by a layer of coupling agent.

FIG. 2 depicts the assembly of FIG. 1 wherein the liquid crystalline diacetylene layer 4 is surmounted by a second substrate 8. In accordance with this embodiment orientation of the diacetylene layer 4 is facilitated by the intermediation of CAM layers 6 and 10. The assembly of FIG. 2 is particularly suited for use as a display device and for many other functions for which liquid crystalline materials are known to be suitable. Polymerization of the diacetylene layer 4 may be had through heating, or, it is believed, by exposure to actinic-radiation. The indicated assembly is thus suitable for use as a waveguide or for other optical, electro-optical, electro-acoustical, etc. uses. Through judicious selection of diacetylenes electro-optical processing, second harmonic generation, and many other useful functions may be performed by the diacetylene layer 4. The material may also be employed as a conductor, insulator, structural laminate or the like.

Figure 3:
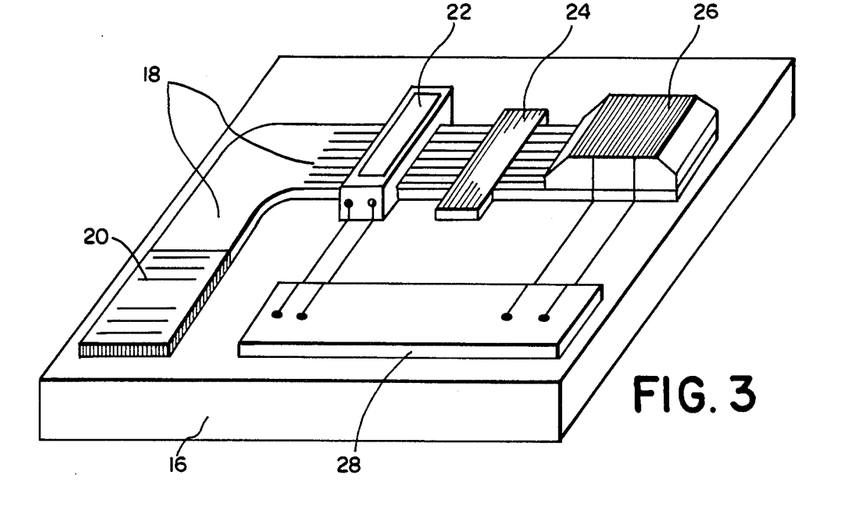
FIG. 3 depicts a schematic representation of certain articles which are among the many useful devices which may be elaborated through employment of one or more embodiments of the present invention.

FIG. 3 depicts an integrated optical circuit which may be prepared employing the embodiments of the present invention. Thus, a substrate "chip" 16 is surmounted by a patterned polymer wave guide 18 derived from the diacetylenes and processing methods of the present invention. A source of a light signal such as a LASER light source 20 is also provided which may similarly be prepared in accordance with the present invention. Electrode array 22, optical components 24, detectors or beam couplers 26 and numerous other optical, electro-optical, electro-acoustic, etc. components may also be included in the device as suggested. Preferably, the components 28 are also incorporated in the device to expedite processing of the optical signals thus generated. As will be appreciated by those of ordinary skill in the art, a very wide variety of optical, electro-optical, electro-acoustical, waveguiding and other circuit elements, devices and assemblages may be prepared in accordance with the present invention.

The following examples are intended to be illustrative only and are not to be construed as limiting.

SYNTHESIS OF MONOVINYL ACETYLENES

EXAMPLE 1

1-(p-tolyl)but-1-en-3-yne

A solution of pyridazine-1-oxide (0.036 mol) in tetrahydrofuran (15 ml) was added dropwise to a stirred solution of the Grignard reagent formed from 0.04 g. atom of magnesium and 0.04 mol. of 4-bromotoluene in tetrahydrofuran (30 ml) maintained at 5° to 15° C. The mixture was stirred at 25° C. for 0.5 hours, then diluted with about 40 ml of 20% hydrochloric acid and extracted three times with 50 ml of ether. The combined ether extracts were washed with sodium bicarbonate solution and water and then dried. The material was filtered, evaporated, chromatographed on silica with n-hexane to give the pure enyne as a red oil (60%).

NMR: 7.1–7.2 (4H, m), 6.9 (d, 1H), 6.0 (dd, 1H), 3.0 (d, 1H), 2.1 (3H, s).

EXAMPLE 2

1-(p-ethylphenyl)but-1-en-3-yne

A solution of 0.018 mol. of pyridazine-1-oxide in 10 ml of tetrahydrofuran was added dropwise to a stirred solution of the Grignard reagent from Mg (0.02 g. atom) and 4-ethylbromobenzene (0.02 mol) in tetrahydrofuran (15 ml) maintained at 5° to 15° C. The mixture was stirred at 25° C. for 0.5 hours, then diluted with about 20 ml of 20% hydrochloric acid and extracted three times with 25 ml of ether. The combined ether extracts were washed with sodium bicarbonate solution and water and dried. Filtration and evaporation followed by chromatography of the residue on silica with n-hexane gave the pure enyne as a golden yellow oil (58%).

NMR: 7.1–7.3 (4H, m), 7.0 (1H, d), 6.1 (1H, dd), 3.0 (1H, d). 2.6 (2H, q), 1.3 (3H, t).

EXAMPLE 3

1-(p-propylphenyl)but-1-en-3-yne

A stirred solution of 0.13 moles of propargyl triphenyl-phosphonium bromide and 0.013 moles of p-propylbenzaldehyde in about 30 ml of acetonitrile was treated with anhydrous ammonia (15–20 ml) at about −50° C. The resulting deep yellow emulsion was stirred for about 4 hours at about −50° C., and at 0° C. for an additional 4 hours, and finally allowed to stand at room temperature overnight. The solution was acidified with dilute phosphoric acid and thrice extracted with ether. The ether extracts were washed with water, combined, dried, filtered and evaporated to give a light orange syrup which was chromatographed on silica. Elution with n-hexane gave the enyne as a yellow oil (31%).

NMR: 0.95 (3H, t), 1.6 (2H, m), 2.5 (2H, t), 3.5 (1H, d), 5.65 (1H, dd), 6.5 (1H, d), 7.3 (4H, m).

EXAMPLE 4

1-(p-nitrophenyl)but-1-en-3-yne

A stirred solution of 0.13 moles of propargyl triphenyl-phosphonium bromide and 0.011 moles of 4-nitrobenzaldehyde in about 33 mol. of acetonitrile was treated with anhydrous ammonia (15–20 ml) at about −50° C. The deep purple reaction mixture was stirred at about −50° C. for about 4 hours, and at 0° C. for an additional 4 hours, then allowed to stand overnight. It was acidified with dilute phosphoric acid and multiply extracted with ethyl acetate. The combined organic extracts were washed with water, dried, filtered and evaporated to give a brown syrup which was chromotographed on silica. Elution with hexane/ethyl acetate gave the enyne as a yellow shining powder (36%; m.p.-68°–70° C.).

NMR: 8.0–8.18 (2H, m), 8.2–8.35 (2H, m), 6.8 (1H, d), 5.9 (1H, dd), 3.47 (1H, d),

COUPLING OF MONOVINYL ACETYLENES

General Procedure for Examples 5–8

To the selected enyne, from Examples 1–4, in absolute ethanol (5 ml), was added about 1 ml of aqueous, saturated ammonium chloride. A catalytic amount of anhydrous cuprous chloride in small portions was then added. The reaction mixture was allowed to stir at room temperature for several hours, at which time the mixture was poured into excess distilled water and acidified with a small amount of dilute HCl. The solid was separated by filtration. The filtrate was extracted with anhydrous ether which was dried, filtered and evaporated to yield a solid residue. All solid residues were combined and recrystallized from suitable solvents. All of the products of Examples 5–7 displayed viscous behavior and optical birefingence typical of liquid crystals.

EXAMPLE 5

P-tolyl-divinyl diacetylene

From 1 g. (7 m.mol.) of enyne from Example 1, 0.540 g. of crude diacetylene was recovered after about 16 hours of reaction at room temperature. The crude was recrystallized from absolute ethanol to yield 0.330 g. of nice yellow needles (about 33% yield). DSC results showed no evidence of starting enyne. The sample exhibited a liquid crystal phase transition in the form of a relatively small endotherm at 174° C., followed by immediate exothermic polymerization.

EXAMPLE 6 p-Ethyl-phenyl-divinyl diacetylene

From 0.56 g. (3.58 m.mol.) of enyne from Example 2, 0.300 g. of crude diacetylene was recovered after about 20 hours of reaction. The crude was recrystallized from absolute ethanol. 0.152 g. of thin yellow needles (about 27.5% yield) were collected. DSC results showed no evidence of enyne starting material. The sample exhibits three liquid crystal phase transitions at 100°, 115° and 130° C. Polymerization occurs at temperatures higher than 140° C.

EXAMPLE 7 p-propyl-phenyl-divinyl diacetylene

Figure 4:
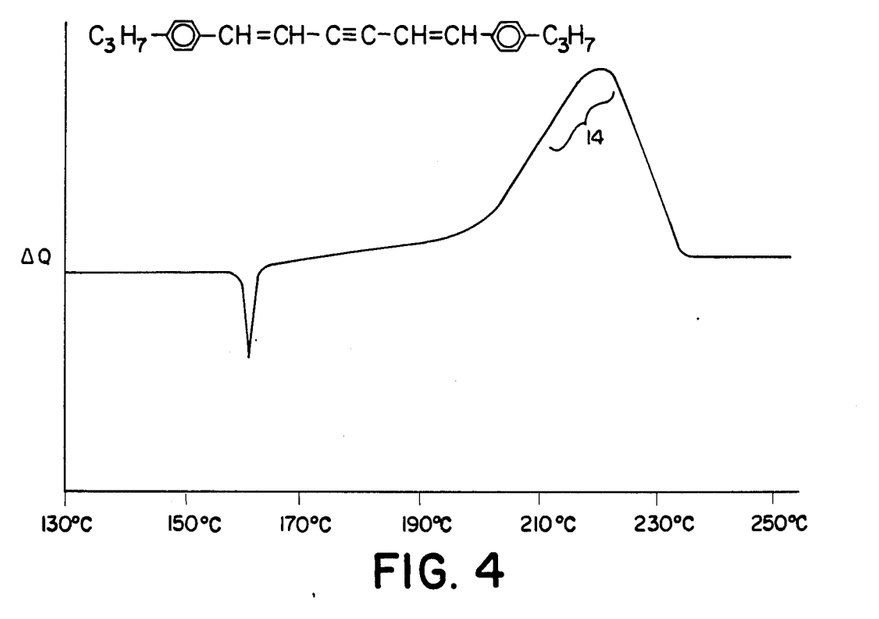
FIG. 4 is a differential scanning calorimetry plot of a diacetylene having a liquid crystalline state.

From 1.18 g. (7.5 m.mol) of enyne from Example 3 reacted for about 24 hours was recovered and 0.480 g. of crude solid was recovered at the end. The crude sample was recrystallized from absolute ethanol and 0.225 g. (about 19% yield) of long, thin, yellow needles were collected. The DSC results are given in FIG. 4 showing a relatively small endotherm at about 156° C. corresponding to the liquid crystal phase transition. The sample slowly polymerized in the liquid crystal state at temperatures over about 165° into an orange-red glassy solid.

EXAMPLE 8 p-Nitro-phenyl-divinyl diacetylene

From 1.2 g. (6.86 m.mol.) or enyne from Example 4 reacted for about 18 hours was recovered 0.280 g. of crude solid. The sample was recrystallized from nitromethane and 0.174 gm of yellowish-orange, small needles (about 14.5% yield) were collected. There was no evidence for starting enyne. The sample melted to the liquid state at about 195° C. and decomposed in the melt over 200° C. without demonstrating liquid crystalline behavior.

COVALENT COUPLING OF LIQUID CRYSTALLINE DIACETYLENES TO SUBSTRATES

EXAMPLE 9

Preparation of Substrates

A silicon substrate having a silicon-dioxide surface of thickness of approximately 5000–6000 Angstroms was cleaned by immersion for 5 minutes in a 50/50 mixture of hydrogen peroxide and sulfuric acid at 70° C. and dried in a nitrogen. The silicon substrate was etched in concentrated nitric acid for about 4 hours at room temperature, washed with ultra-pure distilled water and dried in vacuo.

Aminopropylsilation was effected by treatment of the silicon wafers with vapors of 3-aminopropyltriethoxysilane contained in refluxing xylene. The reaction was performed in a dry nitrogen atmosphere. The wafers were treated in this manner for about 16 hours, rinsed with dry xylene, and dried under nitrogen. The water contact angle of the silanated substrate was 47°±2°. The silanated substrate was immersed in a solution containing 0.075 g. of 10,12-pentacosadiynoic acid (0.20 m.mol.) and 0.052 g of N,N-dicyclohexylcarbodiimide (0.25 m.mol.) in 10 ml of anhydrous pyridine for about 22 hours at room temperature under a nitrogen atmosphere. The wafer was rinsed in pyridine and in ethanol and then dried in vacuo. The water contact angle was found to be 90°±2°.

EXAMPLE 10

It is believed that the foregoing technique of Example 9 may be applied to diacetylenes having liquid crystalline phases. Such diacetylene should be modified to include a carboxylic acid or other suitable group at one terminus to provide a situs for covalent bonding to the aminosilane. In the alternative, other CAMs may be substituted for the aminosilane and other well known procedures employed for the covalent bonding. In addition, surface grooving and non-covalent CAM orientation are believed to be useful for liquid crystal diacetylene orientation.

EXAMPLE 11

The liquid crystalline diacetylenes of Examples 5–7 may be polymerized in the liquid crystal state by heating to the polymerization temperature ascertained from DSC evaluation for from about 5 to about 30 minutes.

What is claimed is:

1. A method for preparing a polymerized article comprising
   providing a substrate,
   placing upon the substrate at least one layer of at least one composition comprising at least one divinyl or dialkenyl diacetylene monomer having a liquid crystalline state,
   causing said layer substantially to assume a liquid crystalline state, and
   imagewise polymerizing the layer while it is substantially in a liquid crystalline state.

2. The method of claim 1 further comprising applying an electric and/or magnetic field to the layer at least prior to said polymerizing step.

3. The method of claim 1 wherein said polymerization is initiated through actinic irradiation.

4. The method of claim 3 wherein said polymerization is initiated by heating.

5. The method of claim 1 wherein the layer is surmounted by a second substrate.

6. The method of claim 1 wherein said layer is substantially oriented inter se.

7. The method of claim 1 wherein said layer is bonded covalently to the substrate.

8. The method of claim 1 wherein at least one diacetylene has the formula:

wherein $R_1$ and $R_2$ may be the same or different and are selected from the group consisting of H, cyano, halogen and alkyl having from 1 to about 3 carbon atoms;
wherein $R_3$ and $R_4$ may be the same or different and are selected from the group consisting of H, cyano, halogen, amino, aryl and alkyl having from 1 to about 6 carbon atoms, and
wherein $R_5$ and $R_6$ may be the same or different and are selected from the group consisting of H, cyano, alkyl, aryl, aralkyl, alkaryl and heterosubstituted alkyl and aryl having from 1 to about 30 carbon atoms.

9. The method of claim 1 wherein at least one diacetylene has the formula:

where $R_7$ and $R_8$ may be the same or different and are selected from the group consisting of H, cyano, halogen, amino, nitro, hydroxyl, sulfoxyl, sulfonyl, and alkyl, aryl, alkaryl or aralkyl having from about 1 to about 24 carbon atoms.

10. The method of claim 1 wherein at least one diacetylene has the formula:

wherein $R_9$ is alkyl having from about 1 to about 24 carbon atoms.

11. The method of claim 1 wherein the polymerized layer has a sensible nonlinear optical effect.

12. The method of claim 1 wherein the composition further comprises a minor porportion of non-liquid crystalline material.

13. The method of claim 1 wherein the diacetylene comprises a dialkenyl diacetylene.

* * * * *